(12) United States Patent
Prasad et al.

(10) Patent No.: US 6,949,513 B2
(45) Date of Patent: Sep. 27, 2005

(54) POLYPEPTIDES OF COVALENTLY LINKED SYNTHETIC BIOACTIVE PEPTIDE ANALOG(S) FOR TREATMENT OF CANCER

(75) Inventors: Sudhanand Prasad, Ghaziabad (IN); Rama Mukherjee, Ghaziabad (IN); Anand C. Burman, Ghaziabad (IN); Archna Mathur, Ghaziabad (IN); Rajan Sharma, Ghaziabad (IN); Manu Jaggi, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 614 days.

(21) Appl. No.: 10/186,226

(22) Filed: Jun. 28, 2002

(65) Prior Publication Data

US 2003/0105009 A1 Jun. 5, 2003

Related U.S. Application Data (60) Provisional application No. 60/308,273, filed on Jul. 27, 2001.

(51) Int. Cl.$^7$ ............................................... A61K 38/00
(52) U.S. Cl. ............................ 514/12; 514/15; 514/16; 530/300; 530/311; 530/327; 530/328
(58) Field of Search ........................... 514/12, 15, 16; 530/327, 328, 300, 311, 332

(56) References Cited

U.S. PATENT DOCUMENTS

2003/0050233 A1 * 3/2003 Burman et al. ............... 514/12

* cited by examiner

*Primary Examiner*—Sheela J. Huff
(74) *Attorney, Agent, or Firm*—Ladas & Parry LLP (57) ABSTRACT

A polypeptide of the formula (I),

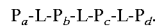
$P_a\text{-L-}P_b\text{-L-}P_c\text{-L-}P_d$.

28 Claims, 2 Drawing Sheets

POLYPEPTIDES OF COVALENTLY LINKED SYNTHETIC BIOACTIVE PEPTIDE ANALOG(S) FOR TREATMENT OF CANCER

This application claims the benefit of U.S. Provisional Application(s) No(s).: APPLICATION NO(S).: 60/308,273 FILING DATE Jul. 27, 2001 and incorporates the same by reference.

FIELD OF THE INVENTION

This invention relates to the synthesis of a polypeptide by covalently linking different bioactive peptide analogs. Bioactive peptide analogs, of known anti cancer activities, are linked together using suitable linkers. The present invention also describes a polypeptide that is synthesized as a precursor molecule, and is processed in a sequence-specific manner to yield the constituent biologically active peptide. The individual peptides are cleaved from the polypeptide by suitable enzyme digestion to exhibit individual, additive and/or synergistic biological activity/functions. The bioactive anti cancer peptide analogs have been selected from analogs of Somatostatin, Substance P, Vasoactive Intestinal Peptide and Bombesin. The polypeptide of the invention may be usefully employed in cancer therapy.

BACKGROUND OF THE INVENTION

Most tumour cells secrete certain growth factors to promote their proliferative activity. Our previous studies (disclosed in U.S. Pat. No. 6,156,725 and Australian Patent No. 707,158) have shown that peptides such as vasoactive intestinal peptide (VIP), somatostatin, bombesin and substance P also have specific high affinity receptors on the tumour cells, to which these peptides bind and which play a key role in cell proliferation. Specially designed analogs to these peptides can abrogate the proliferative effects of these peptides by binding to their receptors. It has also been shown from our studies (U.S. patent application Ser. No. 09/896,903) that when these peptides analogs are used in combination, they exert a synergistic effect, which is greater than when these analogs are used alone.

In our present invention novel conformationally constrained analogs of the above peptides (described in our U.S. Pat. No. 6,316,414 and U.S. patent application Ser. Nos. 09/630,333; 09/630,345 and 09/629,642) are linked together using suitable linkers consisting of pairs of basic amino acids to form a polypeptide. The individual analogs are released from the polypeptide by specific enzymatic cleavage at the linker site in vivo.

Such cleavage at pairs of basic residues is also known in biological systems. Most polypeptide hormones are synthesized as pro-hormones, and undergo endoproteolytic cleavage at pairs of basic residues (Lys-Arg, Arg-Arg) by enzymes called Prohormone Convertases (PCs), to give rise to the active molecule (Wilson, H. E and White, A, Trends Endocrinol. Metab. 1998, 9, 396–402; Jean F et al., Biochem. J. 1993, 292, 891–900, Mitra, J et al, Biochem J. 1998, 334, 275–282).

Of the bioactive peptides mentioned in the invention, Bombesin, is an amphibian peptide that has a structure closely related to that of several mammalian peptides, including Gastrin Releasing Peptide (GRP) and Neuromedins B and C. Bombesin, GRP and related peptides exert their in vivo effects by binding to specific receptors on cells of the gastrointestinal tract, the central nervous system and tumours. It has been reported (J. H. Walsh and J. R. Reeve, Peptides 6, (3), 63–68, (1985) that bombesin and bombesin-like peptides such as gastrin releasing peptide (GRP) are secreted by human small-cell lung cancer (SCLC) cells. It has been postulated (P. J. Woll and E. Rozengurt, PNAS 85, 1859–1863, (1988)) that gastrin releasing factor antagonists would bind competitively to bombesin receptors in animals and would therefore be of use in the treatment of SCLC and/or in the control of clinical symptoms associated with this disease and due to hypersecretion of this peptide hormone. Analogues of bombesin/GRP have been shown to inhibit the binding of gastrin releasing peptide to a SCLC cell line and to inhibit the growth of SCLC cells in-vitro and in-vivo (S. Mahmoud et al., CancerResearch, 1991, 51, 1798; Moody T W et al., Life Sci., 1995, 56, 521; Moody T W et al., Peptides, 1996, 17, 1337). We have designed the conformationally constrained antagonist analogs of bombesin by incorporating α,α-dialkylated amino acids. These antagonist analogs have shown anticancer activity in various cancers described in our U.S. patent application Ser. No. 09/630,633. In this application we have selected one of such antagonist analogs bombesin as component of the novel designed polypeptide.

Vasoactive intestinal peptide (VIP) is a widely distributed peptide hormone which mediates a variety of physiological responses including gastrointestinal secretion, relaxation of gastrointestinal, vascular and respiratory smooth muscle, lipolysis in adipocytes, pituitary hormone secretion, and excitation and hyperthermia after injection into the central nervous system. VIP receptors were characterized and localized in the neoplastic cells of most breast carcinomas, breast cancer metastases, ovarian adenocarcinoma, endometrial carcinomas, prostate cancer metastases, bladder carcinomas, colonic and pancreatic adenocarcinomas, gastrointestinal squamous cell carcinomas, non-small cell lung cancers, lymphomas, astrocytomas, glioblastomas and meningiomas (Reubi J C, (1995) J Nucl. Med., 36 (10):1846–53).

We have shown in our U.S. Pat. No. 6,156,725 that the eight residue VIP receptor binding inhibitor is antiproliferative to various cancers. In this patent application we have used this eight residue peptide as component for the novel designed polypeptide.

Substance P was the first gut neuropeptide discovered. It regulates gastrointestinal motility, increases blood flow in the gut, stimulates secretion of pancreas, salivary glands, small intestines and inhibits acid secretion. (Dockray, G. J., 1994,401 Gut peptides: Biochemistry and Physiology, Raven Press Ltd, New York). The role of Substance P in cancer has been well recognized particularly in small cell lung cancer. Several antagonists such as antagonist A, antagonist D and antagonist G of substance P have been described in literature which show inhibition of SCLC xenografts in vivo. (Wolf P. J. and Rozengurt, E., 1990, Can. Res. 50(13): 3968–73. Reeve, J. G. and Bleehen, N. M. 1994, Biochem. Biophys. Res. Commun. 199(3): 1313–19.)

We have designed the conformationally constrained antagonist analogs of substance P by incorporating α,α-dialkylated amino acids. These antagonist analogs have shown anticancer activity in various cancers described in our U.S. patent application Ser. No. 09/629,642. In this application we have selected one of such antagonist analog of substance P as component of the novel designed polypeptide.

The cyclic tetradecapeptide somatostatin was originally isolated from the hypothalamus and characterized as a physiological inhibitor of growth hormone release from the anterior pituitary. It was characterized by Guillemin et al. and is described in U.S. Pat. No. 3,904,594 (Sep. 9, 1975).

Somatostatin has also been found to regulate insulin, glucagon and amylase secretion from the pancreas, and gastric acid release in the stomach. Its ability to inhibit the secretion of such hormones, allows somatostatin and its analogs to be therapeutically employed in clinical conditions for the treatment of acromegaly, pancreatic islet cell tumours, diabetes mellitus and gastrointestinal bleeding. Somatostatin receptors have been found to be over-expressed in a wide range of tumors, those arising in the brain (including meningioma, astrocytoma, neuroblastoma, hypophysial adenoma, paraganglioma, Merkel cell carcinoma, and gliomas), the digestive-pancreatic tract (including insulinoma, gluconoma, AUODoma, VIPoma, and colon carcinoma), lung, thyroid, mammary gland, prostate, lymphatic system (including both Hodgkin's and non-Hodgkin's lymphomas), and ovaries. It has been shown that somatostatin and some somatostatin analogues are capable of activating the tyrosine phosphatase enzyme, which antagonizes the effect of tyrosine kinases playing a very important role in the tumorous transformation [A. V. Schally: Cancer Res. 48, 6977 (1988)]. The importance of tyrosine kinases is supported by the fact that the majority of oncogenes code for tyrosine kinase and the major part of the growth factor receptors is tyrosine kinase [Yarden et al.: Ann. Rev. Biochem. 57, 443 (1989)].

We have designed the conformationally constrained agonist analogs consisting of eight amino acids of somatostatin by incorporating α,α-dialkylated amino acids. These agonist analogs have shown anticancer activity against various cancers and this is described in our U.S. Pat. No. 6,316,414, the subject matter of which is incorporated by reference. In this application we have selected one of such agonist analog of somatostatin as component of the novel designed polypeptide.

We have previously shown in our U.S. Pat. No. 6,156,725 and Australian patent No. 707,158; that Vasoactive intestinal peptide (VIP), Somatostatin, Substance P and Bombesin are secreted by some human tumor cells and that there are specific high affinity binding sites for these peptides on these cells. The four peptides were also shown to bind to tumor cells. The antagonist/analogs of these peptides were shown to have anti-proliferative activity on certain cancer cells, more specifically adenocarcinomas. A combination of the peptide antagonists/analogs was also shown to cause tumor regression in a nude mice xenograft model. It was hypothesized by us that there exists an autocrine mechanism for cell proliferation where the peptides are secreted by tumor cells and transduce cellular signals through specific cell surface receptors leading to cell proliferation. The analogs/antagonists to these peptides may then abrogate/block these cellular signals linked to proliferation. Further the antiangiogenic potential of the antagonist/analogs has also been described by us previously (U.S. application Ser. No. 09/248,381 and PCT application WO 00/047221).

We have also described in our U.S. Pat. No. 6,316,414 and U.S. patent application (Ser. Nos. 09/630,333; 09/630,345 & 09/629,642) (the subject matter of which is incorporated by reference) novel antiproliferative antagonist analogs of VIP, Bombesin, Substance P and agonist analogs of Somatostatin that are useful in the treatment of cancer. These analogs were designed incorporating α,α-dialkylated amino acids and show antiproliferative activity in a number of human tumor cell lines. Further, they caused partial tumor regression in nude mice xenografts. However, when used individually, these peptides had a narrow spectrum of activity with moderate levels of cytotoxicity. We have previously shown the synergistic in vivo tumor efficacy of these peptides in our U.S. patent application Ser. No. 09/896,903 in which it has been shown that when these peptides were used in combination as a mixture they exert a synergistic biological effect which is greater than the effect produced by any individual peptide alone.

In the present invention we have linked together the four designed peptides analogs of Somatostatin, Bombesin, Substance P and Vasoactive Intestinal Peptide, using a suitable linker, to form a single polypeptide. It is proposed that the individual peptides would be released from the polypeptide by appropriate enzymatic cleavage at the linker site in vivo.

Throughout the specification and claims, the following abbreviations are used with the following meanings:

| | |
|---|---|
| BOP: | Benzotriazole-1-yl-oxy-tris-(dimethylamino)-phosphonium hexofluorophospate |
| PyBOP: | Benzotriazole-1-yl-oxy-tris-pyrrolidino-phosphonium Hexofluorophospate |
| HBTU: | O-Benzotriazole-N,N,N',N'-tetramethyl-uronium-hexofluoro-phosphate |
| TBTU: | 2-(1H-Benzotriazole-lyl)-1,1,3,3-tetramethyluronium tetrafluoroborate |
| HOBt: | 1-Hydroxy Benzotriazole |
| DCC: | Dicyclohexyl carbodiimide |
| DIPCDI: | Diisopropyl carbodiimide |
| DIEA: | Diisopropyl ethylamine |
| DMF: | Dimethyl formamide |
| DCM: | Dichloromethane |
| NMP: | N-Methyl-2-pyrrolidinone |
| TFA: | Trifluoroacetic acid |

In the formula (I) below and throughout the specification, the amino acids residues are designated by their standard abbreviations. Amino acids denote L-configuration unless otherwise indicated by D or DL appearing before the symbol and separated from it by hyphen.

The following abbreviations are used for uncommon amino acids:

Orn=Ornithine

Pen=Penicillamine

Aib=α-Aminoisobutyric acid

Ac5c=1-Aminocyclopentane carboxylic acid

SUMMARY OF THE INVENTION

The present invention comprises polypeptides of the general formula (I), where, $P_a$, $P_b$, $P_c$, and $P_d$ represent any of the peptides P1, P2, P3 or P4;

L represents the linker and may be lysine-lysine, lysine-arginine, arginine-lysine or arginine-arginine linker residues, which are used to link the individual peptides, P1, P2, P3 and P4, in the polypeptide sequence.

One Lys is used as a linker only after the peptide P1 which terminates with Lys so the sequence is Lys-Lys in the final peptide.

The individual peptides, P1, P2, P3 and P4 have the sequences:

P1=Leu-Met-Tyr-Pro-Thr-Tyr-Leu-Lys-OH (SEQ ID NO:1)

P2=D-Phe-Gln-Trp-Ala-Val-Aib-His-Leu-NH$_2$ (SEQ ID NO:2)

P3=D-Arg-Pro-Lys-Pro-D-Phe-Gln-D-Trp-Phe-D-Trp-Leu-Ac5c-NH$_2$ (SEQ ID NO:3)

P4=D-Phe-Cys-Tyr-D-Trp-Orn-Ac5c-Pen-Thr-NH$_2$, (having a disulphide bond between Cys and Pen amino acids) (SEQ ID NO:4).

Each of these peptides have been described individually in U.S. patent application Ser. Nos. 09/630,333; 09/630,345; 09/629,642 and 09/629,371, the subject matter of which is incorporated by reference.

The polypeptides described herein are designed to be hydrolyzed by suitable enzymatic cleavage and ultimately release the component peptides in vivo.

DETAILED DESCRIPTION OF THE INVENTION

The polypeptides of the present invention have the general formula (I)

P$_a$-L-P$_b$-L-P$_c$-L-P$_d$, where,

P$_a$, P$_b$, P$_c$, and P$_d$ represent any of the peptides P1, P2, P3 or P4;

L represents the linker and may be lysine-lysine, lysine-arginine, arginine-lysine or arginine-arginine linker residues, used to link the individual peptides, P1, P2, P3 and P4, in the peptide polypeptide sequence.

One Lys is used as a linker only after the peptide P1 which terminates with Lys so the sequence is Lys-Lys in the final peptide.

The individual peptides, P1, P2, P3 and P4 have the sequences:

P1=Leu-Met-Tyr-Pro-Thr-Tyr-Leu-Lys-OH (SEQ ID NO:1)

P2=D-Phe-Gln-Trp-Ala-Val-Aib-His-Leu-NH$_2$ (SEQ ID NO:2)

P3=D-Arg-Pro-Lys-Pro-D-Phe-Gln-D-Trp-Phe-D-Trp-Leu-Ac5c-NH$_2$ (SEQ ID NO:3)

P4=D-Phe-Cys-Tyr-D-Trp-Orn-Ac5c-Pen-Thr-NH$_2$, (a disulphide bond between Cys and Pen amino acids) (SEQ ID NO:4).

The pharmaceutically acceptable salt of any of the peptides may be used.

The "pharmaceutically acceptable salt" refer to nontoxic salts of the compounds of this invention. Representative salts and esters include but are not limited to the following: acetate, ascorbate, benzoate, citrate, oxalate, stearate, trifluoroacetate, succinate, tartarate, lactate, fumarate, gluconate, glutamate, phosphate/diphosphate, and valerate. Other salts include Ca, Li, Mg, Na, and K salts, halides, salts of amino acids such as lysine or arginine; guanidine, ammonium, substituted ammonium salts or aluminium salts. The salts of the peptides are prepared by conventional methods.

Suitable routes of administration are those known in the art and include, oral, rectal, transdermal, vaginal, transmucosal or intestinal administration; parenteral delivery, including intramuscular, subcutaneous, intramedullary injections, as well as intrathecal, direct intraventricular, intravenous, intraperitoneal, intranasal, or intraocular injections.

Pharmaceutical compositions suitable for use in the present invention include compositions wherein the active ingredients are contained in an effective amount to achieve its intended purpose.

The methods of this invention comprise, consist of, or consist essentially of: administering systemically to the mammal a therapeutically effective quantity of any of the mentioned peptides SEQ ID:5 to SEQ ID:10. An effective dose ranges form 0.01 to 4.0 mg of the peptides per kg of the body weight of the mammal, with the dose dependent on the effects sought, the manner of administration, the peptides selected, and the cancer being treated. Systemic administration refers to oral, rectal, nasal, transdermal, and parental (i.e., intramuscular, intravenous and subcutaneous). In accordance with good clinical practice, it is preferred to administer the composition at a dose that will produce anticancer effects without causing undue harmful side effects. The composition may be administered either alone or as a mixture with other therapeutic agents.

The term "an effective amount" means the amount of the drug or pharmaceutical agent that will elicit the biological or medical response of a tissue system, animal or human that is being sought.

In addition to the active ingredients, these pharmaceutical compositions containing one or more of the polypeptides may contain suitable pharmaceutically acceptable carriers, excipients, diluents, solvents, flavorings, colorants etc. The preparations may be formulated in any form including but not limited to tablets, capsules, powders, syrups, suspensions, slurries, time release formulations, sustained release formulations, pills, granules, emulsions, patches, injections, solutions, liposomes and nanoparticles.

The composition may optionally and preferably contain pharmaceutically acceptable diluents, excipients, solvents, binders, stabilizers, and the like. Such diluents may include: RPMI 1649, buffered saline, isotonic NaCl, Ringer's solution, water, distilled water, polyethylene glycol (neat or in water), 2% Tween in water, dimethylsulfoxide to 50% in water, propylene glycol (neat or in water), phosphate buffered saline, balanced salt solution, glycerol, and other conventional fluids that are suitable for intravenous administration. Pharmaceutical composition which provide from about 1.0 to 10.0 mg of the composition per unit dose are preferred and are conventionally prepared as tablets, lozenges, capsules, powders, aqueous or oily suspension, syrups, elixirs, and aqueous solutions. The nature of the pharmaceutical composition employed will, of course, depend on the desired route of administration.

The exact formulation, route of administration and dosage can be chosen by the individual physician in view of the patient's condition.

Toxicity and therapeutic efficacy of the peptide and polypeptides of this invention can be determined by standard pharmaceutical procedures including testing in cell cultures or in animals.

The preferred novel polypeptides of the present invention have the sequence of peptides in the order indicated in each sequence id.

P4-Lys-Lys-P3-Lys-Lys-P1-Lys-P2 (SEQ ID NO: 5)
P4-Lys-Lys-P1-Lys-P2-Lys-Lys-P3 (SEQ ID NO: 6)
P3-Lys-Lys-P2-Lys-Lys-P1-Lys-P4 (SEQ ID NO: 7)
P4-Lys-Arg-P3-Lys-Arg-P1-Lys-P2 (SEQ ID NO: 8)
P4-Arg-Lys-P3-Arg-Lys-P1-Lys-P2 (SEQ ID NO: 9)
P4-Arg-Arg-P3-Arg-Arg-P1-Lys-P2 (SEQ ID NO: 10)

The novel polypeptides of the present invention have shown anti cancer activity in vitro and in vivo experiments, the details of which are described in the subsequent section of examples in this patent application.

The polypeptides described herein are designed to be hydrolyzed by suitable enzymatic cleavage and ultimately release the component peptides in vivo. The ability of the polypeptides to release the corresponding linear peptides has been evaluated in vitro. The disappearance of the polypeptide, and the appearance of the constituent linear peptides was monitored by Reverse Phase HPLC and molecular mass determination by MALDI-MS.

Synthesis of Polypeptides

The novel polypeptides of the present invention can be made exclusively by solid phase techniques, by a combination of solution phase and solid phase techniques, or, by fragment condensation. These methods for the chemical synthesis of polypeptides are well known in the art (Stewart and Young, 1969). Preferred, semi-automated, stepwise solid phase methods for synthesis of peptides of the invention are provided in the examples discussed in a subsequent section of this document.

In a preferred embodiment of the present invention the peptides were synthesized using Fmoc strategy on a semi-automatic peptide synthesizer (CS Bio, Model 536), using optimum side chain protection. The peptides were assembled from C-terminus to N-terminus. The loading of the first Fmoc protected amino acid was achieved via an amide bond formation with the solid support mediated by diisopropyl carbodiimide (DIPCDI) and HOBt. Substitution levels for automated synthesis were preferably between 0.2 and 0.8 mmole amino acid per gram resin.

The resin employed for the synthesis of carboxy-terminal amidated peptide analogs was 4-(2',4'-Dimethoxyphenyl-Fmoc-aminomethyl)-phenoxymethyl-derivatized polystyrene 1% divinylbenzene (Rink Amide) resin (100–200 mesh), procured from Advanced Chemtech, Louisville, Ky., U.S.A., (0.6 milliequivalent NH. sub. 2/g resin).

In a particularly preferred embodiment of the present invention the following chemical moieties were used to protect reactive side chains of the peptides during the synthesis procedure.

The N-terminal amino group was protected by 9-flourenylmethoxy-carbonyl (Fmoc) group. Trityl or acetamidomethyl (Acm) were the preferred protecting groups for cysteine and penicillamine was preferably protected with the acetamidomethyl (Acm) group. Boc was the preferred side-chain protecting group for lysine and ornithine. Tyrosine and threonine were used with t-butyl (tBu) protection whereas Pmc (Pentamethyl chroman-6-sulphonyl) or Pbf (2,2,4,6,7-pentamethyldihydrobenzofuran-5-sulphonyl) were the preferred protecting groups for arginine. The side chain of glutamine was preferably protected with trityl (Trt) protecting group, whereas histidine was used with Boc or trityl (Trt) protection.

In a preferred embodiment of the invention, 2–8 equivalents of Fmoc protected amino acid per resin nitrogen equivalent was used. The activating reagents used for coupling amino acids to the resin in solid phase peptide synthesis, are well known in the art and include DCC or DIPCDI/HOBt, BOP, PyBOP, HBTU, and TBTU. Preferably, DCC or DIPCDI/HOBt or HBTU/HOBT and DIEA were used as activating reagents in the coupling reactions. The coupling reaction was carried out in DMF, DCM or NMP or a mixture of these solvents and was monitored by Kaiser test [Kaiser et al., Anal. Biochem., 34, 595–598 (1970)]. In case of a positive Kaiser test, the appropriate amino acid was re-coupled using freshly prepared activated reagents.

After the assembly of the peptide chain was completed, disulfide bond formation was either carried out on-resin, where the Acm side-chain protecting groups were removed using iodine in dimethylformamide, and the free thiol groups thus generated were oxidized simultaneously to yield the cyclized peptide. The peptide-resin was then washed with methanol and dried. Where post-cleavage disulphide formation was carried out, the N-terminal Fmoc group was removed and the peptide was cleaved from the resin support by treatment with a cleavage mixture consisting of trifluoroacetic acid, ethanedithiol and de-ionized water for 1 to 4 hours at room temperature. Normally, the cleavage mixture also simultaneously removed the side-chain protecting groups, except for the side-chain protecting Acm groups that were not removed by the above procedure. The crude peptide was obtained by precipitation with cold dry ether, filtered, dissolved, and lyophilized. Where disulfide formation was carried out on the crude Acm-protected peptide, the Acm group was removed by any of the known methods such as using thallium trifluoroacetate, iodine etc.

The resulting crude peptide was purified by preparative high performance liquid chromatography using C-18 reverse phase column, on a preparative HPLC system (Shimadzu Corporation, Japan) using a gradient of 0.1% TFA in acetonitrile and water. The eluted fractions were reanalyzed on analytical HPLC system (Shimadzu Corporation, Japan) using a C18 reverse-phase column. acetonitrile was evaporated and the fractions were lyophilized to obtain the pure peptide. The identity of each peptide was confirmed by MALDI-MS (matrix assisted laser desorbtion/ionization mass spectrometry)

The present invention has been described in detail with reference to the following examples, as will be appreciated by a person skilled in the art, is merely illustrative, and should not be construed as limiting. Various other modifications of the invention will be possible without departing from the spirit and scope of the present invention.

EXAMPLE 1

Synthesis of SEQ ID NO: 5

P4-Lys-Lys-P3-Lys-Lys-P1-Lys-P2

The polypeptide, P4-Lys-Lys-P3-Lys-Lys-P1-Lys-P2 (SEQ. ID. NO: 5), a forty residue peptide amide, was synthesized, preferably by solid phase peptide synthesis, on semi-automated peptide synthesizer (CS Bio, California, USA) using solid phase Fmoc/tBu chemistry. Synthesis was carried out on 0.6 mM scale. The Fmoc amino acids were used in 2–5 fold molar excess. Coupling was carried out in DIPCDI/HOBt or in HBTU/DIEA. Alternate coupling and deprotection steps were checked for completion by negative and positive Kaiser test respectively. The double coupling (e.g. the coupling reaction was repeated twice) was carried out for coupling of an unusual amino acid.

Upon completion of synthesis, deprotection of the N-terminal amino acid was carried out in 20% piperidine in dimethylformamide for 30 min. The peptide was cleaved from the resin in a cleavage mixture consisting of crystalline phenol, 1,2-ethanedithiol, thioanisole, distilled water and trifluoroacetic acid. The cleavage time varied between 2 to 5 hours. The peptide was filtered from the resin and precipitated with cold dry ether, dissolved in water and lyophilized. The crude peptide thus obtained was subsequently analyzed on analytical HPLC system and purified on a preparative HPLC system (Shimadzu Corporation, Japan), using a C-18 reverse phase column, using a gradient of 0.1%

TFA in acetonitrile and water. Correct molecular mass was obtained for the purified peptide by LC-MS, before S-S (mass=5330) and after disulfide formation (observed mass=5187) by conventional methods using Iodine or thallium trifluoroacetate.

Trypsin Digestion

The polypeptides of the present invention are designed to be cleaved enzymatically by enzyme trypsin, ultimately releasing the constituent linear peptide fragments.

From our studies we found that on incubation of the polypeptide with the enzyme trypsin (1:25, w/w) at 37° C. and pH 8.0–8.5, the peptide disappeared completely in ~5 hours and formed cleavage products. On controlled digestion of the polypeptide peptide (SEQ ID NO:5), with enzyme trypsin, for ~15 minutes, 3 major peaks were identifiable on analytical HPLC.

Briefly, the peptide was weighed, dissolved in $NH_4HCO_3$ buffer (pH 8.0) and mixed with freshly made enzyme trypsin (1 mg/ml in water) in a ratio of 1:25 (w/w) of enzyme: substrate, according to published protocol (Ref.: Methods in Mol. Bio., Vol. 32, Basic protein and peptide protocols, Enzymatic methods for cleaving proteins). The digestion mixture was incubated at 37° C. Aliquots were taken at different time points and analyzed on analytical HPLC (Shimadzu, Japan). The 15' enzyme digest sample was picked up for analysis by MALDI-MS.

MALDI-MS Data of Trypsin Digest of Polypeptide (SEQ ID NO:5)

Figure 1:
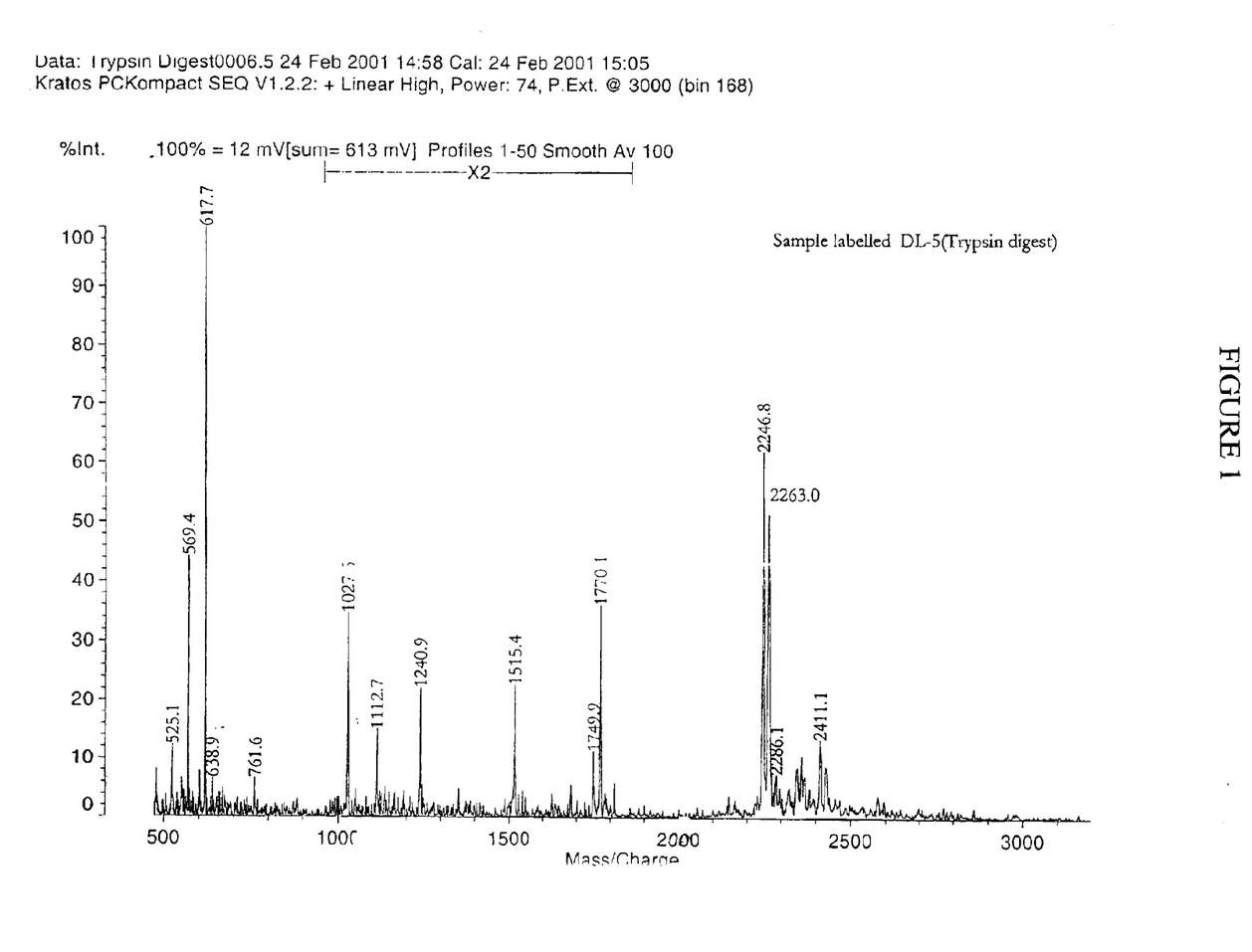
FIG. 1 is the MALDI-MS profile of polypeptide (SEQ ID NO:5)

The 15 minutes trypsin digest sample of the polypeptide (SEQ ID NO:5) was diluted 1:1 (v/v) with acetonitrile and analyzed by MALDI-MS. The profile on MALDI mass spectrometer is shown in FIG. 1.

The following peptides were identifiable:

Peptide P1 at molecular mass=1027.5;

Peptide (P2+Lys) at molecular mass=1112.7;

Peptide (P2+Lys+Lys) at molecular mass=1240.9;

Peptide P3 at molecular mass=1515.4;

Peptide (P3+Lys+Lys) at molecular mass=1770.1; and,

Fragment (1–4) of peptide P4 without the Acm at mass=617.7.

All the four constituent peptides of the polypeptide peptide, (SEQ.I.D.NO:5), were identifiable in the MALDI-MS spectra of the 15' trypsin digest. Only residue (1–4) of peptide P4 was obtained, i.e., there is cleavage at the D-Trp-Orn bond. Cleavage at Trp-X bond is typical of chymotrypsin-like enzyme activity, and, it is known that enzyme trypsin also undergoes autolysis in these conditions (pH 8.0 and 37° C.), to produce (among other products), ψ-trypsin, which has chymotrypsin-like activity. X in Trp-X bond refers to any amino acid following trytophan in a polypeptide sequence. This may contribute towards low-frequency, "nontryptic" cleavages, at some tyrosyl, phenylalanyl, or tryptophanyl bonds. The literature claims that low levels of $Ca^{2+}$(0.1 mM $CaCl_2$) added to digestion buffers may reduce production of ψ-trypsin by autolysis.

EXAMPLE 2

Synthesis of SEQ ID NO: 6

P4-Lys-Lys-P1-Lys-P2-Lys-Lys-P3

The synthetic strategy followed for the above polypeptide sequence was similar to that carried out for (SEQ ID NO: 5) in the example above. The crude polypeptide was purified on preparative HPLC and correct molecular mass (Calculated Mass=5188.56; Observed Mass=5187) was obtained by LC-MS.

EXAMPLE 3

Synthesis of SEQ ID NO: 7

P3-Lys-Lys-P2-Lys-P1-Lys-Lys-P4

The synthetic strategy followed for the above polypeptide sequence, on a 0.072 mM scale, was similar to that carried out for (SEQ ID NO: 5) in the example above and 0.325 g of the polypeptide on resin was obtained. The peptide was cleaved from the resin as in Example 1 above. The crude polypeptide was purified on preparative HPLC, as above, and characterized using MALDI-MS. Correct molecular mass was obtained for the purified peptide by MALDI before S-S (observed mass=5330) and after disulfide formation (observed mass=5187). The disulphide bond formation was carried out by conventional methods using Iodine or thallium trifluoroacetate.

EXAMPLE 4

In vitro Activity of Peptides

SEQ ID NO: 5 and SEQ ID NO: 7 were tested for cytotoxicity against 6 human tumor cell lines. Briefly, a three day MTT cytotoxicity assay was performed, which is based on the principle of uptake of MTT (3-(4,5-dimethylthiazol-2-yl)-2,5-diphenyl tetrazolium bromide), a tetrazolium salt, by the metabolically active cells where it is metabolized by active mitochondria into a blue colored formazan product that is read spectrophoto-metrically. MTT was dissolved in phosphate buffered saline with a pH of 7.4 to obtain an MTT concentration of 5 mg/ml; the resulting mixture was filtered through a 0.22 micron filter to sterilize and remove a small amount of insoluble residue. For each type of tumor cell, 20,000 to 50,000 cells were seeded in a 96-well culture plate and incubated with the drug in a $CO_2$ incubator for 72 hours. The final concentration range of SEQ ID NO: 5 and SEQ ID NO: 7 was 1 nM to 10 μM. The drug was added at time 0, 24 and 48 hours. Control cells not treated with the drug were similarly incubated. The assay was terminated after 72 hours by adding 100 ug (20 ul) of MTT to each well, then incubating for additional one hour, and finally adding 50 ul of 10% SDS-0.01N HCl to each well to lyse the cells and dissolve formazan. After incubating for one hour, the plate was read spectrophotometrically at 540 nm and the cyto-toxicity percentage calculated. The following Tables 1 and 2 show the dose response of SEQ ID NO: 5 and SEQ ID NO: 7 respectively along with their respective $ED_{50}$ values on different tumor cell lines.

TABLE 1

Dose response and $ED_{50}$ values of SEQ ID NO: 5 on human tumor cell lines

| Cell line | Percent cytotoxicity | | | | | $ED_{50}$ ($\mu$M) |
|---|---|---|---|---|---|---|
| | 1 nM | 10 nM | 100 nM | 1 $\mu$M | 10 $\mu$M | |
| KB (Oral) | 10.6 ± 1.2 | 18.2 ± 1.9 | 30.7 ± 3.9 | 43.1 ± 5.3 | 98.3 ± 5.7 | 2.1 |
| MiaPaCa.2 (Pancreas) | 24.2 ± 2.7 | 37.8 ± 4.6 | 48.2 ± 4.8 | 59.6 ± 4.9 | 84.5 ± 6.3 | 0.210 |
| PTC (Colon) | 16.5 ± 1.6 | 14.2 ± 2.2 | 16.8 ± 1.0 | 21.7 ± 2.9 | 27.9 ± 2.8 | >10 |
| L132 (Lung) | 20.5 ± 3.2 | 21.5 ± 3.9 | 22.2 ± 2.8 | 28.2 ± 3.1 | 48.8 ± 3.6 | 0.13 |
| MCF-7 (Breast) | 29.7 ± 3.8 | 28.2 ± 4.3 | 35.3 ± 4.8 | 59.4 ± 4.8 | 85.4 ± 5.0 | 0.34 |
| MOLT-4 (Leukemia) | 10.4 ± 0.7 | 18.7 ± 1.9 | 34.7 ± 4.7 | 54.3 ± 5.2 | 94.5 ± 6.1 | 0.29 |

TABLE 2

Dose response and $ED_{50}$ values of SEQ ID NO: 7 on human tumor cell lines

| Cell line | Percent cytotoxicity | | | | | $ED_{50}$ ($\mu$M) |
|---|---|---|---|---|---|---|
| | 1 nM | 10 nM | 100 nM | 1 $\mu$M | 10 $\mu$M | |
| KB (Oral) | 13.9 ± 1.9 | 23.9 ± 1.8 | 34.8 ± 3.9 | 54.3 ± 5.8 | 82.8 ± 5.4 | 0.75 |
| MiaPaCa.2 (Pancreas) | 24.9 ± 2.8 | 22.9 ± 1.4 | 23.8 ± 2.9 | 28.8 ± 1.9 | 27.8 ± 2.8 | >10 |
| PTC (Colon) | 13.5 ± 1.8 | 18.7 ± 0.5 | 23.5 ± 3.5 | 28.5 ± 2.1 | 17.9 ± 1.9 | >10 |
| L132 (Lung) | 9.0 ± 0.6 | 10.4 ± 0.4 | 13.3 ± 0.1 | 14.9 ± 0.6 | 23.1 ± 0.9 | >10 |
| MCF-7 (Breast) | 18.9 ± 2.0 | 19.0 ± 0.5 | 22.9 ± 1.4 | 23.6 ± 2.9 | 31.4 ± 3.7 | >10 |
| MOLT-4 (Leukemia) | 23.7 ± 1.6 | 34.9 ± 4.9 | 46.0 ± 4.9 | 54.3 ± 4.9 | 88.5 ± 6.8 | 0.19 |

EXAMPLE 5

Pharmaceutical Composition and Therapeutic Dose of Claimed Polypeptides

An example within the scope of the invention comprises of peptides of SEQ ID NO: 5 to SEQ ID NO: 10. The molar concentration of each of the peptides where it is expected to be active ranges from $10^{-4}$ M to $10^{-10}$ M. However, it is expected that these peptides would be effective if the concentration of each ranged from approximately $10^{-5}$ M to approximately $10^{-9}$ M.

A formulation of each of these peptides for in vitro use may be prepared in the following way. A stock solution of each of the peptide is prepared with a pH of approximately 7.0 to approximately 7.4. Although sterile phosphate buffered saline was used to prepare the stock solutions for the testing described below, other diluents may be used such as RPMI 1640, buffered saline, isotonic NaCl, Ringer's solution, water (for injection), distilled water, polyethylene glycol (neat or in water), 2% Tween in water, dimethylsulfoxide to 50% in water, propylene glycol (neat or in water), balanced salt solution, glycerol, and other conventional fluids that are suitable for intravenous administration. To obtain a pH in the range of approximately 7.0 to 7.4 for each stock solution, the pH can be adjusted by using 1N HCL for lowering the pH or 1N NaOH for raising the pH, although other conventional agents for adjusting the pH can be used. The concentration of the peptide is approximately $10^{-3}$ M. This is further diluted using the above-mentioned diluents to give a final concentration of $10^{-8}$ M. In one exemplary embodiment, the pH of the peptide solution may range from approximately 7.0 to approximately 7.4. To obtain a pH in this range, the pH can be adjusted by using 1N HCL for lowering the pH or 1N NaOH for raising the pH, although other conventional agents or adjusting the pH can be used.

EXAMPLE 6

The Antitumor Activity of SEQ ID:5 and SEQ ID:7 on PTC (Colon) Tumor Xenografts Grown in Nude Mice PTC (colon) tumor xenografts were initiated in Balb/c athymic mice by subcutaneous inoculation of a single cell suspension of PTC cells($15 \times 10^6$ cells/100 L). When the average tumor volume reached around 2000 mm³ the tumor-bearing mice were divided into three groups of 3 animals each. Two groups were randomly assigned for SEQ ID NO: 5 and SEQ ID NO: 7 treatment while the third group served as control. SEQ ID NO: 5 and SEQ ID NO:7 were prepared at a concentration of 250 $\mu$g/ml so as to deliver a dose of 50 $\mu$g per 200 $\mu$l. The injections were given twice a day at 12 hour intervals so as to deliver a total dose of 100 $\mu$g. The treatment was continued daily for a period of 14 days. The anti-tumor activity of SEQ ID NO: 5 and SEQ ID NO: 7 was monitored by measuring tumor volumes every fourth day and calculating volumes using the formula $0.4 \times W^2 \times L$ (W=smaller dia, L=larger dia,).

Figure 2:
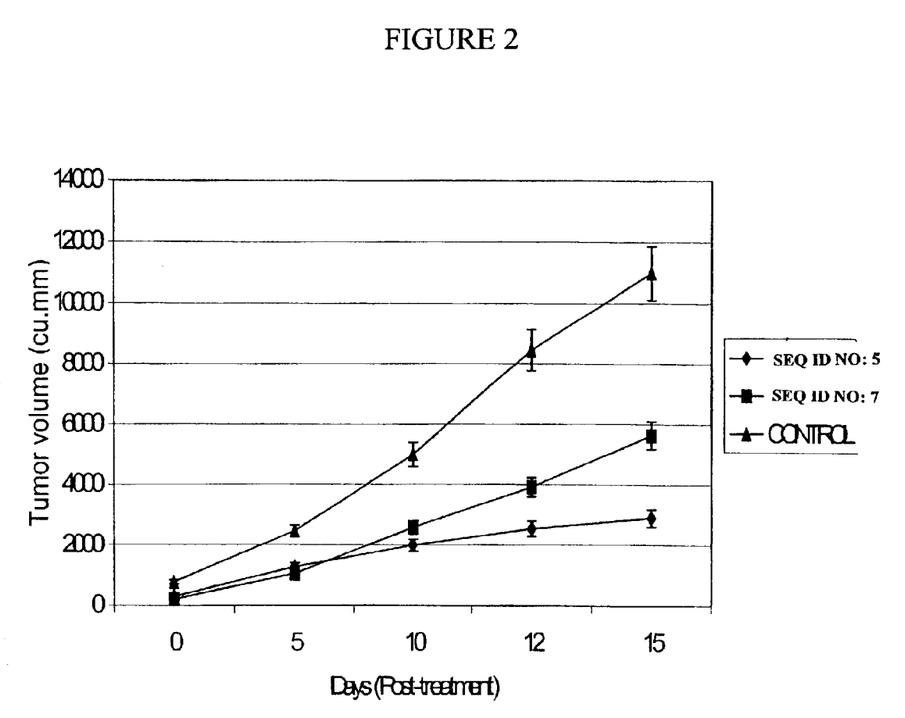
FIG. 2 shows the tumor regression of PTC (colon) tumor xenografts.

Tumor regression of 73.7% and 48.7% was caused in SEQ ID NO:5 and SEQ ID NO: 7 treated tumor-bearing mice respectively as compared to untreated mice. This is shown in the FIG. 2.

What is claimed is:

1. A polypeptide of the formula (I), $P_a$-L-$P_b$-L-$P_c$-L-$P_d$, where, $P_a$, $P_b$, $P_c$, and $P_d$ represent any of the peptides P1, P2, P3 or P4 or a pharmaceutically acceptable salt thereof;

L is a linker used to link the peptides and is selected from the group consisting of lysine, lysine-lysine, lysine-arginine, arginine-lysine and arginine-arginine;

wherein,

P1 is Leu-Met-Tyr-Pro-Thr-Tyr-Leu-Lys (SEQ ID NO: 1)

P2 is D-Phe-Gln-Trp-Ala-Val-Aib-His-Leu (SEQ ID NO: 2)

P3 is D-Arg-Pro-Lys-Pro-D-Phe-Gln-D-Trp-Phe-D-Trp-Leu-Ac5c (SEQ ID NO: 3) and

P4 is D-Phe-Cys-Tyr-D-Trp-Orn-Ac5c-Pen-Thr, having a disulphide bond between Cys and Pen amino acids (SEQ ID NO: 4).

2. The polypeptide of the claim 1, wherein $P_a$ is P4, $P_b$ is P3, $P_c$ is P1 and $P_d$ is P2; and said polypeptide is P4-Lys-Lys-P3-Lys-Lys-P1-Lys-P2 (SEQ ID NO:5).

3. The polypeptide of the claim 1, wherein $P_a$ is P4, $P_b$ is P1, $P_c$ is P2 and $P_d$ is P3; and said polypeptide is P4-Lys-Lys-P1-Lys-P2-Lys-Lys-P3 (SEQ ID NO:6).

4. The polypeptide of the claim 1, wherein $P_a$ is P3, $P_b$ is P2, $P_c$ is P1 and $P_d$ is P4; and said polypeptide is P3-Lys-Lys-P2-Lys-Lys-P1-Lys-P4 (SEQ ID NO:7).

5. The polypeptide of the claim 1, wherein $P_a$ is P4, $P_b$ is P3, $P_c$ is P1 and $P_d$ is P2; and said polypeptide is P4-Lys-Arg-P3-Lys-Lys-P1-Lys-P2 (SEQ ID NO:8).

6. The polypeptide of the claim 1, wherein $P_a$ is P4, $P_b$ is P3, $P_c$ is P1 and $P_d$ is P2; and said polypeptide is P4-Arg-Lys-P3-Arg-Lys-P1-Lys-P2 (SEQ ID NO:9).

7. The polypeptide of the claim 1, wherein $P_a$ is P4, $P_b$ is P3, $P_c$ is P1 and $P_d$ is P2; and said polypeptide is P4-Arg-Arg-P3-Arg-Arg-P1-Lys-P2 (SEQ ID NO:10).

8. A composition comprising a polypeptide of formula (I), where,
- $P_a$, $P_b$, $P_c$, and $P_d$ represent any of the peptides P1, P2, P3 or P4 or a pharmaceutically acceptable salt thereof;
- L is a linker used to link the peptides and is selected from the group consisting of lysine, lysine-lysine, lysine-arginine, arginine-lysine and arginine-arginine, wherein,
- P1 is Leu-Met-Tyr-Pro-Thr-Tyr-Leu-Lys (SEQ ID NO: 1)
- P2 is D-Phe-Gln-Trp-Ala-Val-Aib-His-Leu (SEQ ID NO: 2)
- P3 is D-Arg-Pro-Lys-Pro-D-Phe-Gln-D-Trp-Phe-D-Trp-Leu-Ac5c (SEQ ID NO: 3) and
- P4 is D-Phe-Cys-Tyr-D-Trp-Orn-Ac5c-Pen-Thr, having a disulphide bond between Cys and Pen amino acids (SEQ ID NO: 4) and a diluent, excipient, solvent, binder or stabilizer.

9. The composition according to claim 8 wherein the polypeptide is P4-Lys-Lys-P3-Lys-Lys-P1-Lys-P2 (SEQ ID NO:5).

10. The composition of claim 8, wherein the polypeptide is P4-Lys-Lys-P1-Lys-P2-Lys-Lys-P3 (SEQ ID NO:6).

11. The composition of claim 8, wherein the polypeptide is P3-Lys-Lys-P2-Lys-Lys-P1-Lys-P4 (SEQ ID NO:7).

12. The composition of claim 8, wherein the polypeptide is P4-Lys-Arg-P3-Lys-Lys-P1-Lys-P2 (SEQ ID NO:8).

13. The composition of claim 8, wherein the polypeptide is P4-Arg-Lys-P3-Arg-Lys-P1-Lys-P2 (SEQ ID NO:9).

14. The composition of claim 8, wherein the polypeptide is P4-Arg-Arg-P3-Arg-Arg-P1-Lys-P2 (SEQ ID NO:10).

15. A method for treating cancer or a tumor comprising administering an effective amount of a polypeptide of the formula (I)

where,
- $P_a$, $P_b$, $P_c$, and $P_d$ represent any of the peptides P1, P2, P3 or P4 or a pharmaceutically acceptable salt thereof;
- L is a linker used to link the peptides and is selected from the group consisting of lysine, lysine-lysine, lysine-arginine, arginine-lysine or arginine-arginine wherein,
- P1 is Leu-Met-Tyr-Pro-Thr-Tyr-Leu-Lys (SEQ ID NO: 1)
- P2 is D-Phe-Gln-Trp-Ala-Val-Aib-His-Leu (SEQ ID NO: 2)
- P3 is D-Arg-Pro-Lys-Pro-D-Phe-Gln-D-Trp-Leu-Ac5c (SEQ ID NO: 3) and
- P4 is D-Phe-Cys-Tyr-D-Trp-Orn-Ac5c-Pen-Thr, having a disulphide bond between Cys and Pen amino acids (SEQ ID NO: 4).

16. The method of claim 15, wherein $P_a$ is P4, $P_b$ is P3, $P_c$ is P1 and $P_d$ is P2; and the polypeptide is P4-Lys-Lys-P3-Lys-Lys-P1-Lys-P2 (SEQ ID NO:5).

17. The method of claim 15, wherein $P_a$ is P4, $P_b$ is P1, $P_c$ is P2 and $P_d$ is P3; and the polypeptide is P4-Lys-Lys-P1-Lys-P2-Lys-Lys-P3 (SEQ ID NO:6).

18. The method of claim 15, wherein $P_a$ is P3, $P_b$ is P2, $P_c$ is P1 and $P_d$ is P4; and the polypeptide is P3-Lys-Lys-P2-Lys-Lys-P1-Lys-P4 (SEQ ID NO:7).

19. The method of claim 15, wherein $P_a$ is P4, $P_b$ is P3, $P_c$ is P1 and $P_d$ is P2; and the polypeptide is P4-Lys-Arg-P3-Lys-Arg-P1-Lys-P2 (SEQ ID NO:8).

20. The method of claim 15, wherein $P_a$ is P4, $P_b$ is P3, $P_c$ is P1 and $P_d$ is P2; and the polypeptide is P4-Arg-Lys-P3-Arg-Lys-P1-Lys-P2 (SEQ ID NO:9).

21. The method of claim 15, wherein $P_a$ is P4, $P_b$ is P3, $P_c$ is P1 and $P_d$ is P2; and the polypeptide is P4-Arg-Arg-P3-Arg-Arg-P1-Lys-P2 (SEQ ID NO:10).

22. The method according to claim 15, wherein the cancer is oral, pancreatic, colon, lung, breast or leukemia.

23. The method of claim 16, wherein the cancer is oral, pancreatic, colon, lung, breast or leukemia.

24. The method of claim 17, wherein the cancer is oral, pancreatic, colon, lung, breast or leukemia.

25. The method according to claim 18, wherein the cancer is oral, pancreatic, colon, lung, breast or leukemia.

26. The method of claim 19, wherein the cancer is oral, pancreatic, colon, lung, breast or leukemia.

27. The method of claim 20, wherein the cancer is oral, pancreatic, colon, lung, breast or leukemia.

28. The method according to claim 21, wherein the cancer is oral, pancreatic, colon, lung, breast or leukemia.

* * * * *

SEQUENCE LISTING

<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: This peptide was synthetically generated

<400> SEQUENCE: 1

Leu Met Tyr Pro Thr Tyr Leu Lys
1               5

<210> SEQ ID NO 2
<211> LENGTH: 8
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (6)..(6)
<223> OTHER INFORMATION: /product = Alpha-amino-isobutyric acid/label =
      Aib

<400> SEQUENCE: 2

Xaa Gln Trp Ala Val Xaa His Leu
1               5

<210> SEQ ID NO 3
<211> LENGTH: 11
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Arginine/label = D-Arg
<220> FEATURE:
<221> NAME/KEY: MISC_FEATURE
<222> LOCATION: (5)..(5)
<223> OTHER INFORMATION: /product = D-Phenylalanine/label = D-Phe
<220> FEATURE:
<221> NAME/KEY: MISC_FEATURE
<222> LOCATION: (7)..(7)
<223> OTHER INFORMATION: /product = D-Tryptophan/label = D-Trp
<220> FEATURE:
<221> NAME/KEY: MISC_FEATURE
<222> LOCATION: (9)..(9)
<223> OTHER INFORMATION: /product = D-Tryptophan/label = D-Trp
<220> FEATURE:
<221> NAME/KEY: MISC_FEATURE
<222> LOCATION: (11)..(11)
<223> OTHER INFORMATION: /product = 1-Aminocyclopentance carboxylic
      acid/label = Ac5c

<400> SEQUENCE: 3

Xaa Pro Lys Pro Xaa Gln Xaa Phe Xaa Leu Xaa
1               5                   10

<210> SEQ ID NO 4
<211> LENGTH: 8
<212> TYPE: PRT
<213> ORGANISM: Artificial Sequence
<220> FEATURE:

```
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (4)..(4)
<223> OTHER INFORMATION: /product = D-Tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (6)..(6)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (7)..(7)
<223> OTHER INFORMATION: /product = Penicillamine/label = Pen

<400> SEQUENCE: 4

Xaa Cys Tyr Xaa Xaa Xaa Xaa Thr
1               5

<210> SEQ ID NO 5
<211> LENGTH: 40
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (4)..(4)
<223> OTHER INFORMATION: /product = D-Tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (6)..(6)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (7)..(7)
<223> OTHER INFORMATION: /product = Penicillamine/label = Pen
<220> FEATURE:
<221> NAME/KEY: MISC_FEATURE
<222> LOCATION: (11)..(11)
<223> OTHER INFORMATION: /product = D-Arginine/label = D-Arg
<220> FEATURE:
<221> NAME/KEY: MISC_FEATURE
<222> LOCATION: (15)..(15)
<223> OTHER INFORMATION: /product = D-Phenylalanine/label = D-Phe
<220> FEATURE:
<221> NAME/KEY: MISC_FEATURE
<222> LOCATION: (17)..(17)
<223> OTHER INFORMATION: /product = D-Tryptophan/label = D-Trp
<220> FEATURE:
<221> NAME/KEY: MISC_FEATURE
<222> LOCATION: (19)..(19)
<223> OTHER INFORMATION: /product = D-Tryptophan/label = D-Trp
<220> FEATURE:
<221> NAME/KEY: MISC_FEATURE
<222> LOCATION: (21)..(21)
<223> OTHER INFORMATION: /product = 1-Aminocyclopentane carboxylic acid/
      label = Ac5c
<220> FEATURE:
<221> NAME/KEY: MISC_FEATURE
```

```
<222> LOCATION: (33)..(33)
<223> OTHER INFORMATION: /product = D-Phenylalanine/label = D-Phe
<220> FEATURE:
<221> NAME/KEY: MISC_FEATURE
<222> LOCATION: (38)..(38)
<223> OTHER INFORMATION: /product = Alpha-amino-isobutyric acid/label =
      Aib

<400> SEQUENCE: 5

Xaa Cys Tyr Xaa Xaa Xaa Xaa Thr Lys Lys Xaa Pro Lys Pro Xaa Gln
1               5                   10                  15

Xaa Phe Xaa Leu Xaa Lys Lys Leu Met Tyr Pro Thr Tyr Leu Lys Lys
            20                  25                  30

Xaa Gln Trp Ala Val Xaa His Leu
        35                  40

<210> SEQ ID NO 6
<211> LENGTH: 40
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (4)..(4)
<223> OTHER INFORMATION: /product = D-Tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (6)..(6)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (7)..(7)
<223> OTHER INFORMATION: /product = Penicillamine/label = Pen
<220> FEATURE:
<221> NAME/KEY: MISC_FEATURE
<222> LOCATION: (20)..(20)
<223> OTHER INFORMATION: /product = D-Phenylalanine/label = D-Phe
<220> FEATURE:
<221> NAME/KEY: MISC_FEATURE
<222> LOCATION: (25)..(25)
<223> OTHER INFORMATION: /product = Alpha-amino-iosbutyric acid/label =
      Aib
<220> FEATURE:
<221> NAME/KEY: MISC_FEATURE
<222> LOCATION: (30)..(30)
<223> OTHER INFORMATION: /product = D-Arginine/label = D-Arg
<220> FEATURE:
<221> NAME/KEY: MISC_FEATURE
<222> LOCATION: (34)..(34)
<223> OTHER INFORMATION: /product = D-Phenylalanine/label = D-Phe
<220> FEATURE:
<221> NAME/KEY: MISC_FEATURE
<222> LOCATION: (36)..(36)
<223> OTHER INFORMATION: /product = D-Tryptophan/label = D-Trp
<220> FEATURE:
<221> NAME/KEY: MISC_FEATURE
<222> LOCATION: (38)..(38)
<223> OTHER INFORMATION: /product = D-Tryptophan/label = D-Trp
<220> FEATURE:
<221> NAME/KEY: MISC_FEATURE
<222> LOCATION: (40)..(40)
<223> OTHER INFORMATION: /product = 1-Aminocyclopentance carboxylic
      acid/label = Ac5c

<400> SEQUENCE: 6
```

Xaa Cys Tyr Xaa Xaa Xaa Xaa Thr Lys Lys Leu Met Tyr Pro Thr Tyr
1               5                   10                  15

Leu Lys Lys Xaa Gln Trp Ala Val Xaa His Leu Lys Lys Xaa Pro Lys
            20                  25                  30

Pro Xaa Gln Xaa Phe Xaa Leu Xaa
        35              40

<210> SEQ ID NO 7
<211> LENGTH: 40
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Arginine/label = D-Arg
<220> FEATURE:
<221> NAME/KEY: MISC_FEATURE
<222> LOCATION: (5)..(5)
<223> OTHER INFORMATION: /product = D-Phenylalanine/label = D-Phe
<220> FEATURE:
<221> NAME/KEY: MISC_FEATURE
<222> LOCATION: (7)..(7)
<223> OTHER INFORMATION: /product = D-Tryptophan/label = D-Trp
<220> FEATURE:
<221> NAME/KEY: MISC_FEATURE
<222> LOCATION: (9)..(9)
<223> OTHER INFORMATION: /product = D-Tryptophan/label = D-Trp
<220> FEATURE:
<221> NAME/KEY: MISC_FEATURE
<222> LOCATION: (11)..(11)
<223> OTHER INFORMATION: /product = 1-Aminocyclopentance carboxylic acid/
      label = Ac5c
<220> FEATURE:
<221> NAME/KEY: MISC_FEATURE
<222> LOCATION: (14)..(14)
<223> OTHER INFORMATION: /product = product/ = D-Phenylalanine/label =
      D-Phe
<220> FEATURE:
<221> NAME/KEY: MISC_FEATURE
<222> LOCATION: (19)..(19)
<223> OTHER INFORMATION: /product = Alpha amino-isobutyric acid/label =
      Aib
<220> FEATURE:
<221> NAME/KEY: MISC_FEATURE
<222> LOCATION: (33)..(33)
<223> OTHER INFORMATION: /product = D-Phenylalanine/label = D-Phe
<220> FEATURE:
<221> NAME/KEY: MISC_FEATURE
<222> LOCATION: (36)..(36)
<223> OTHER INFORMATION: /product = D-Tryptophan/label = D-Trp
<220> FEATURE:
<221> NAME/KEY: MISC_FEATURE
<222> LOCATION: (37)..(37)
<223> OTHER INFORMATION: /product = Ornithine/label = Orn
<220> FEATURE:
<221> NAME/KEY: MISC_FEATURE
<222> LOCATION: (38)..(38)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (39)..(39)
<223> OTHER INFORMATION: /product = Penicillamine/label = Pen

<400> SEQUENCE: 7

Xaa Pro Lys Pro Xaa Gln Xaa Phe Xaa Leu Xaa Lys Lys Xaa Gln Trp
1               5                   10                  15

Ala Val Xaa His Leu Lys Lys Leu Met Tyr Pro Thr Tyr Leu Lys Lys
            20                  25                  30

```
Xaa Cys Tyr Xaa Xaa Xaa Xaa Thr
        35                  40

<210> SEQ ID NO 8
<211> LENGTH: 40
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (4)..(4)
<223> OTHER INFORMATION: /product = D-Tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (6)..(6)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (7)..(7)
<223> OTHER INFORMATION: /product = Penicillamine/label = Pen
<220> FEATURE:
<221> NAME/KEY: MISC_FEATURE
<222> LOCATION: (11)..(11)
<223> OTHER INFORMATION: /product = D-Arginine/label = D-Arg
<220> FEATURE:
<221> NAME/KEY: MISC_FEATURE
<222> LOCATION: (15)..(15)
<223> OTHER INFORMATION: /product = D-Phenylalanine/label = D-Phe
<220> FEATURE:
<221> NAME/KEY: MISC_FEATURE
<222> LOCATION: (17)..(17)
<223> OTHER INFORMATION: /product = D-Tryptophan/label = D-Trp
<220> FEATURE:
<221> NAME/KEY: MISC_FEATURE
<222> LOCATION: (19)..(19)
<223> OTHER INFORMATION: /product = D-Tryptophan/label = D-Trp
<220> FEATURE:
<221> NAME/KEY: MISC_FEATURE
<222> LOCATION: (21)..(21)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (33)..(33)
<223> OTHER INFORMATION: /product = D-Phenylalanine/label = D-Phe
<220> FEATURE:
<221> NAME/KEY: MISC_FEATURE
<222> LOCATION: (38)..(38)
<223> OTHER INFORMATION: /product = Alpha amino-isobutyric acid/label =
      Aib

<400> SEQUENCE: 8

Xaa Cys Tyr Xaa Xaa Xaa Xaa Thr Lys Arg Xaa Pro Lys Pro Xaa Gln
1               5                  10                  15

Xaa Phe Xaa Leu Xaa Lys Arg Leu Met Tyr Pro Thr Tyr Leu Lys Lys
            20                  25                  30

Xaa Gln Trp Ala Val Xaa His Leu
        35                  40

<210> SEQ ID NO 9
<211> LENGTH: 40
<212> TYPE: PRT
<213> ORGANISM: Artificial Sequence
```

```
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (4)..(4)
<223> OTHER INFORMATION: /product = D-Tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (6)..(6)
<223> OTHER INFORMATION: /product = 1-Aminocyclopentance carboxylic
     acid/label = Ac5c
<220> FEATURE:
<221> NAME/KEY: MISC_FEATURE
<222> LOCATION: (7)..(7)
<223> OTHER INFORMATION: /product = Penicillamine/label = Pen
<220> FEATURE:
<221> NAME/KEY: MISC_FEATURE
<222> LOCATION: (11)..(11)
<223> OTHER INFORMATION: /product = D-Arginine/label = D-Arg
<220> FEATURE:
<221> NAME/KEY: MISC_FEATURE
<222> LOCATION: (15)..(15)
<223> OTHER INFORMATION: /product = D-Phenylalanine/label = D-Phe
<220> FEATURE:
<221> NAME/KEY: MISC_FEATURE
<222> LOCATION: (17)..(17)
<223> OTHER INFORMATION: /product = D-Tryptophan/label = D-Trp
<220> FEATURE:
<221> NAME/KEY: MISC_FEATURE
<222> LOCATION: (19)..(19)
<223> OTHER INFORMATION: /product = D-Tryptophan/label = D-Trp
<220> FEATURE:
<221> NAME/KEY: MISC_FEATURE
<222> LOCATION: (21)..(21)
<223> OTHER INFORMATION: /product = 1-Aminocyclopentane carboxylic
     acid/label = Ac5c
<220> FEATURE:
<221> NAME/KEY: MISC_FEATURE
<222> LOCATION: (33)..(33)
<223> OTHER INFORMATION: /product = D-Phenylalanine/label = D-Phe
<220> FEATURE:
<221> NAME/KEY: MISC_FEATURE
<222> LOCATION: (38)..(38)
<223> OTHER INFORMATION: /product = Alpha amino-isobutyric acid/label =
     Aib

<400> SEQUENCE: 9

Xaa Cys Tyr Xaa Xaa Xaa Xaa Thr Arg Lys Xaa Pro Lys Pro Xaa Gln
 1               5                  10                  15

Xaa Phe Xaa Leu Xaa Arg Lys Leu Met Tyr Pro Thr Tyr Leu Lys Lys
            20                  25                  30

Xaa Gln Trp Ala Val Xaa His Leu
        35                  40

<210> SEQ ID NO 10
<211> LENGTH: 40
<212> TYPE: PRT
<213> ORGANISM: Artificial Sequence
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-Phenylalanine/label = D-Phe
<220> FEATURE:
<221> NAME/KEY: MISC_FEATURE
<222> LOCATION: (4)..(4)
```

```
<223> OTHER INFORMATION: /product = D-Tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (6)..(6)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (7)..(7)
<223> OTHER INFORMATION: /product = Penicillamine/label = Pen
<220> FEATURE:
<221> NAME/KEY: MISC_FEATURE
<222> LOCATION: (11)..(11)
<223> OTHER INFORMATION: /product = D-Arginine/label = D-Arg
<220> FEATURE:
<221> NAME/KEY: MISC_FEATURE
<222> LOCATION: (15)..(15)
<223> OTHER INFORMATION: /product = D-Phenylalanine/label = D-Phe
<220> FEATURE:
<221> NAME/KEY: MISC_FEATURE
<222> LOCATION: (17)..(17)
<223> OTHER INFORMATION: /product = D-Tryptophan/label = D-Trp
<220> FEATURE:
<221> NAME/KEY: MISC_FEATURE
<222> LOCATION: (19)..(19)
<223> OTHER INFORMATION: /product = D-Tryptophan/label = D-Trp
<220> FEATURE:
<221> NAME/KEY: MISC_FEATURE
<222> LOCATION: (21)..(21)
<223> OTHER INFORMATION: /product = 1-Aminocyclopentane carboxylic acid/
      label = Ac5c
<220> FEATURE:
<221> NAME/KEY: MISC_FEATURE
<222> LOCATION: (33)..(33)
<223> OTHER INFORMATION: /product = D-Phenylalanine/label = D-Phe
<220> FEATURE:
<221> NAME/KEY: MISC_FEATURE
<222> LOCATION: (38)..(38)
<223> OTHER INFORMATION: /product = Alpha-amino isobutyric acid/label =
      Aib

<400> SEQUENCE: 10

Xaa Cys Tyr Xaa Xaa Xaa Xaa Thr Arg Arg Xaa Pro Lys Pro Xaa Gln
1               5                   10                  15

Xaa Phe Xaa Leu Xaa Arg Arg Leu Met Tyr Pro Thr Tyr Leu Lys Lys
            20                  25                  30

Xaa Gln Trp Ala Val Xaa His Leu
        35                  40
```